United States Patent [19]

Schmid

[11] Patent Number: 5,223,569

[45] Date of Patent: Jun. 29, 1993

[54] SELF-ADHESIVE CONDUCTIVE ELASTIC GEL

[75] Inventor: Walter Schmid, Pfaffenhofen/Roth, Fed. Rep. of Germany

[73] Assignee: Zimmer Elektromedizin GmbH, Neu-Ulm, Fed. Rep. of Germany

[21] Appl. No.: 829,080

[22] PCT Filed: Jul. 3, 1990

[86] PCT No.: PCT/EP90/01064

§ 371 Date: Feb. 14, 1992

§ 102(e) Date: Feb. 14, 1992

[87] PCT Pub. No.: WO92/01026

PCT Pub. Date: Jan. 23, 1992

[51] Int. Cl.$^5$ .............................. C08L 3/12; A61B 5/04
[52] U.S. Cl. ..................................... 524/734; 524/47; 525/54.31; 523/105; 427/118; 128/640
[58] Field of Search ............... 524/734, 47; 525/54.31; 523/105; 427/118; 128/640

[56] References Cited

U.S. PATENT DOCUMENTS

| | | | |
|---|---|---|---|
| 4,352,359 | 10/1982 | Larimore et al. | 128/640 |
| 4,560,724 | 12/1985 | Brabetz et al. | 524/734 |
| 5,004,767 | 4/1991 | Krause et al. | 524/734 |
| 5,124,076 | 6/1992 | Smuckler | 128/640 |

FOREIGN PATENT DOCUMENTS 57-049431 3/1982 Japan.

Primary Examiner—Paul R. Michl
Assistant Examiner—LaVonda DeWitt
Attorney, Agent, or Firm—Herbert Dubno

[57] ABSTRACT

A self-adhesive conductive elastic gel which is obtained by polymerization of skin-tolerable polymers or copolymers producing acrylic acid group containing monomers or monomer mixtures in an electrolyte-containing solution of a skin-tolerable starch material. This gel is primarily introduced into body electrodes as the skin-contacting conductive material and is better than known gels in that it provides a better adhesive effect upon reproducible use.

7 Claims, No Drawings

SELF-ADHESIVE CONDUCTIVE ELASTIC GEL

CROSS REFERENCE TO RELATED APPLICATION

This application is a national phase of PCT/EP90/01064 filed 3 Jul. 1990.

FIELD OF THE INVENTION

My present invention relates to a self-adhesive conductive elastic gel which is used especially for the production of body electrodes.

BACKGROUND OF THE INVENTION

From German open application 36 09 137 films of electrically conductive polymers are known which can be used as electrode materials. These films contain 0.1 to 50 weight-% of water soluble, substantially acid-group-free polymers, which can be present in the form of cellulose ethers and cellulose. These films are produced by an electrochemical polymerization of the monomers on flat etectrodes in aqueous electrolyte solvents. Thereafter, the films are removed from the electrodes upon which they were deposited.

In German open application 27 40 270, an electrode for medicinal purposes is described, especially for the taking of electrocardiograms, which has as a skin-contacting conductive self-adhesive gel, a hydrophilic polysaccharide like karaya-gum.

The known gels are relatively costly and must be introduced into or applied to the body electrode in a hot state in a technically complex manner. The adhesive capacity thereof against the skin, especially after multiple applications, leaves much to be desired.

OBJECT OF THE INVENTION

The object of the invention is to provide a gel for body electrodes, which avoids the disadvantages of the known gels, which can be simply and economically produced, which has a better adhesive force even after multiple uses than the known gels, and which does not require introduction into a body electrode in a hot state or application in an optional layer to the body electrode.

DESCRIPTION OF THE INVENTION

These objects are achieved with a self-adhesive conductive elastic gel based upon a water-soluble polymer and water-soluble monomers which is obtained by the polymerization of acrylic acid group containing monomers or acrylic acid group containing monomer mixtures with formation of skin-tolerable polymers or copolymers in an electrolyte-containing solution of a skin-tolerable starch material.

The gel can make use of amylopectin and starch material. It can use acrylic acid or methacrylic acid or esters thereof or their precursors. The solution of the starch material can contain a moisture-retaining agent, a pH-increasing substance, and/or a free radical supplying initiator or a photoinitiator for the polymerization of the monomers.

The skin-tolerable salt can be present as an electrolyte. The aqueous solution can contain 10 to 50 weight % of the starch material, 10 to 50 weight % of the monomer or monomers, 3 to 10 weight % of an electrolyte and 1 to 2 weight % of a free radical supplying initiator and the balance to 100% of water.

The invention also relates to the use of the gel of the invention as a self-adhesive conductive elastic material for body electrodes.

The invention is based upon the surprising discovery that when an acrylic acid group containing monomer or an acrylic acid group containing monomer mixture is polymerized to a skin-tolerable polymer or copolymer in a solution of a starch material, a gel is formed that has better adhesive characteristics against the skin even with multiple uses than the hitherto known gels.

Furthermore, it is possible according to the invention to introduce the solution of the starch material prior to the polymerization of a monomer or monomers into a body electrode or to apply them to a body electrode in a cold state and then carry out the polymerization for formation of the gel.

The aqueous solution of a starch material which is used to produce the gel of the invention is an aqueous solution and the monomers introduced for polymerization are also water soluble.

The starch materials which are used are preferably amylopectins with molecular weights between 300,000 and 2,000,000. The starch materials can also be substituted in various ways.

As monomers which are polymerized in the solution of the starch material, acrylic acid group containing monomers or acrylic acid group containing monomer mixtures are used which are polymerizable preferably by free radical generating substances or irradiation like UV radiation, electron irradiation, beta radiation or gamma radiation.

Preferably used as monomers are acrylic acid or methacrylic acid or esters thereof like allylacrylate. One can also introduce precursors for such polymerizable monomers into the polymerizing solution, like for example beta-hydroxypropionic acid which is transformed by heating into acrylic acid which then polymerizes.

Preferably the solution of the starch material in which the named monomers are polymerized, contains a moisture-retaining agent which simultaneously can serve as a plasticizer and for increasing the tackiness. For this purpose suitable substances are polyvalent [polyhydric] alcohols, such as diols, triols and polyols, especially propane triol and glycerine. Furthermore, to the solution of the starch material, a pH-value increasing agent like alkanolamine can be added.

As already indicated, the polymerization can be initiated by substances supplying free radicals. As such substances effective for chemically initialing polymerization, the usual compounds used for this purpose, like per-compounds come to mind.

The polymerization can also be initiated by radiation whereby, in this case, the solution of the starch material preferably employs a photoinitiator known per se and whose selection depends upon the radiation used.

The gel of the invention after its production in corresponding size, can be introduced into body electrodes known per se as the skin-contacting conductive self-adhesive layer in a suitable way although the polymerization of the monomers in the solution of the starch material is effected in situ in or on the electrode. For this purpose a solution of the starch material is produced which, apart from an electrolyte and if desired, a moisture-retaining medium and a substance increasing the pH value, also contains, depending upon the type of polymerization, a free radical supplying compound or photo initiator, whereby to this solution, a solution of the monomer or monomers to be polymerized can be added. The resulting mixture is then applied to or applied in an electrode and polymerized either by the effect of heat or of radiation.

As electrolytes, according to the invention, preferably skin-tolerable salts are used, for example alkali chlorides, such as potassium chloride.

Advantageously, the solution in which the polymerization is effected, contains 10 to 50 weight % of the starch material, 10 to 50 weight % of the monomer or monomers, 3 to 10 weight % of an electrolyte and 1 to 2 weight % of an initiator as well as 10 to 50 weight % of a moisture-retaining medium, the amount being completed to 100%. If desired, the water of an aqueous solution can be completely replaced by the moisture-retaining medium, for example, glycerine.

By selection and concentration of the starch material used and the acrylic acid group containing monomers to be polymerized, as well as the degree of polymerization to which the polymerization is carried out, the gel of the invention can be provided with the desired characteristics, especially with respect to its consistency and adhesive abilities.

SPECIFIC EXAMPLES

The following examples clarify the invention.

EXAMPLE 1

15 weight % distilled water and 35 weight % propanediol are mixed together. 3 weight % potassium chloride is then dissolved in the resulting mixture. Thereafter 5 weight % amylopectin is added and dissolved at a temperature of 90° C. with stirring.

After the amylopectin has gone into solution, the mixture is cooled to 40° C., whereupon 33.7 weight % β-hydroxypropionic acid is added. The temperature is then raised with stirring to 50° C. which has the result of transforming the hydroxy propionic acid into acrylic acid. Then the mixture is cooled to 25° C., whereupon 8 weight % of triethanolamine is added with slow stirring. Then 2 weight % of an acrylated benzophenone is supplied as an initiator with stirring.

The mixture is slowly stirred at a temperature of 20° C. over a period of 3 hours with exclusion of light. Thereafter, the mixture is polymerized on a siliconized foil coated in a layer thickness of 2 mm with UV radiation with a wavelength of 300 nm at a distance of 250 mm over a time period of 30 seconds.

The electrical conductivity value (impedance) AC-Z at 10 Hz of the resulting gel was 240 ohms. The pH value was determined to be 4.8 and the gel to have skin compatibility.

EXAMPLE 2

100 weight % of distilled water and 20 weight % of propanediol are mixed together. 10 weight % of potassium chloride is dissolved in the mixture. Thereafter 20 weight % amylopectin is added with stirring and heated to 90° C. until the amylopectin has dissolved. The resulting solution (solution 1) is then cooled to 20° C. 30 weight % of propanetriol and 30 weight % of solution 1 are mixed together. Thereafter, 2 weight % of ethyleneglycoldimethacrylate and 10 weight % of triethanolamine are added with stirring at a constant temperature of 20° C. Thereafter, under slow stirring, 15 weight % of acrylic acid is dripped into the mixture over a time period of 20 minutes. At a temperature of 50° C., also under stirring, 0.5 weight % of potassiumpersulfate is added in dissolved form and polymerization carried out for 1 hour.

The resulting gel has an electrical conductivity value (impedance) AC-Z at 10 Hz of 260 ohms. The pH value was determined to be 4.5, and in addition, it was determined that the gel was skin compatible.

I claim:

1. A solid self-adhesive conductive elastic gel formed by radiation-induced polymerization of acrylic-acid-group-containing monomers or monomer mixtures in the presence of amylopectin in a conductivity-producing-electrolyte-containing solution to form a skin-tolerable polymer or copolymer.

2. The solid self-adhesive conductive elastic gel defined in claim 1 wherein:
    said acrylic-acid-group-containing monomers or monomer mixtures include beta-hydroxypropionic acid, acrylic acid, methacrylic acid or esters thereof;
    the solution in which polymerization is carried out contains a moisture-retaining compound in the form of glycerine;
    the solution in which polymerization is carried out contains a pH-increasing compound in the form of an alkanolamine;
    the solution in which polymerization is carried out contains a photoinitiator;
    the solution in which polymerization is carried out contains as conductivity producing salts substantially exclusively alkali chlorides; and
    the amylopectin has a molecular weight between substantially 300,000 and 2,000,000.

3. The solid self-adhesive conductive elastic gel defined in claim 1 wherein said solution consists essentially of:
    10 to 50% by weight of said amylopectin;
    10 to 50% by weight of said acrylic-acid-group-containing monomers or monomer mixtures;
    3 to 10% by weight of said conductivity producing salts;
    1 to 2% by weight of said photoinitiator; and
    balance glycerine or glycerine and water to 100%.

4. A method of making a solid self-adhesive conductive elastic gel which comprises the steps of:
    forming a conductivity-producing-electrolyte-containing solution of acrylic-acid-group-containing monomers or monomer mixtures in the presence of amylopectin; and
    radiation-polymerizing said acrylic-acid-group-containing monomers or monomer mixtures in the presence of amylopectin in said solution to form a skin-tolerable polymer or copolymer.

5. The method defined in claim 4 wherein:
    said acrylic-acid-group-containing monomers or monomer mixtures include beta-hydroxypropionic acid, acrylic acid, methacrylic acid or esters thereof;
    the solution in which polymerization is carried out contains a moisture-retaining compound in the form of glycerine;
    the solution in which polymerization is carried out contains a pH-increasing compound in the form of an alkanolamine;
    the solution in which polymerization is carried out contains a photoinitiator;
    the solution in which polymerization is carried out contains as conductivity producing salts substantially exclusively alkali chlorides; and the amylopectin has a molecular weight between substantially 300,000 and 2,000,000.

6. The method defined in claim 5 wherein said solution consists essentially of:

10 to 50% by weight of said amylopectin;

10 to 50% by weight of said acrylic-acid-group-containing monomers or monomer mixtures;

3 to 10% by weight of said conductivity producing salts;

1 to 2% by weight of said photoinitiator; and balance glycerine or glycerine and water to 100%.

7. A method of making a body electrode capable of repeated reuse applications to skin of human bodies, said method comprising the steps of:

making a solid self-adhesive conductive elastic gel by:
  forming a conductivity-producing-electrolyte-containing solution of acrylic-acid-group-containing monomers or monomer mixtures in the presence of amylopectin, and
  radiation-polymerizing said acrylic-acid-group-containing monomers or monomer mixtures in the presence of amylopectin in said solution to form a skin-tolerable polymer or copolymer; and
incorporating said solid self-adhesive conductive elastic gel in a body-electrode support.

* * * * *